(12) United States Patent
Kuhn et al.

(10) Patent No.: US 8,623,346 B1
(45) Date of Patent: Jan. 7, 2014

(54) ANIMAL ATTRACTANT COMPOSITIONS, DEVICES, SYSTEMS AND METHODS

(76) Inventors: Todd Kuhn, North East, MD (US); Joseph J. Gizdic, III, Roadhouse, IL (US)

( * ) Notice: Subject to any disclaimer, the term of this patent is extended or adjusted under 35 U.S.C. 154(b) by 0 days.

(21) Appl. No.: 13/591,819

(22) Filed: Aug. 22, 2012

Related U.S. Application Data

(63) Continuation-in-part of application No. 12/653,447, filed on Dec. 14, 2009, now abandoned.

(51) Int. Cl.
*A01N 65/00* (2009.01)
*A01M 31/06* (2006.01)

(52) U.S. Cl.
USPC .................. 424/84; 119/711; 424/765; 43/2

(58) Field of Classification Search
USPC .......................................... 424/765
See application file for complete search history.

(56) References Cited

U.S. PATENT DOCUMENTS

| 7,814,700 | B2 | 10/2010 | Groth |
| 8,092,789 | B1 | 1/2012 | Teal |
| 2005/0074431 | A1* | 4/2005 | Martin et al. ............... 424/93.4 |
| 2006/0127355 | A1 | 6/2006 | Ainsley |
| 2007/0042077 | A1* | 2/2007 | Morrell et al. .................... 426/2 |
| 2007/0199228 | A1 | 8/2007 | Johnson |
| 2007/0243239 | A1 | 10/2007 | Lanser |

OTHER PUBLICATIONS

Besser, "How Game Animals See & Smell", ATSKO/SNO-SEAL Inc., pp. 1-16, 1993.*
Benetex OB Optical Brightener, Fluorescent Whitening Agent, Mayzo, 2005, pp. 1-5.
High Performance Care for Clothing, Footwear, and More, Atsko, retrieved on Mar. 1, 2012, retrieved from http://www.atsko.com/index.php?option=com_tienda&view=products&filter_category=18.

* cited by examiner

*Primary Examiner* — David J Blanchard
*Assistant Examiner* — John P Nguyen
(74) *Attorney, Agent, or Firm* — Brian S. Steinberger; Law Offices of Brian S. Steinberger, P.A.

(57) ABSTRACT

Animal attractant compositions, devices, systems and methods that can be deployed to attract game animals, such as deer by stimulating several of the animal's senses to attract animals to a desired location. The invention can use a combination of ultraviolet brighteners for visual interest and one or more of deer urine based scents, foods, mineral or salt. The invention capitalizes on the link between many animals' ability to see ultraviolet light with their desire to visualize urine territory markers left by other animals of the same species.

10 Claims, No Drawings

ANIMAL ATTRACTANT COMPOSITIONS, DEVICES, SYSTEMS AND METHODS

CROSS REFERENCE TO RELATED APPLICATIONS

This invention is a Continuation-In-Part of U.S. patent application Ser. No. 12/653,447 filed Dec. 14, 2009, by the same inventors of the subject invention.

FIELD OF INVENTION

This invention relates to the field of hunting game animals, and more specifically to animal attractant compositions, devices, systems and methods to attract game animals by stimulating several of the animal's senses.

BACKGROUND AND PRIOR ART

In the past, science has discovered that some animals possess vision capable of detecting light both in the visible spectrum (~400 to ~700 nanometers wavelength) and the near ultraviolet (~200 to ~400 nanometers wavelength). The evolutionary advantages afforded by this ability are varied. Many fruits, flowers, and seeds are more prominent when viewed in ultraviolet light as compared with normal visible wavelengths. Insects use ultraviolet emissions from stars and the moon to aid in flight navigation. The blood and urine of some animals is easily detected using ultraviolet light.

Various fabric dyes have been found to "glow" when viewed with ultraviolet light and are undesirable in hunting applications. Clothing treated with such dyes, including clothing that appears camouflaged when viewed in visible light, has been found to be unsuitable for hunters. Hunters wearing such clothing appears as a bright, moving beacon to game animals. Calling attention to oneself in such a manner often frightens game animals causing them to flee from the hunter.

Common household laundry detergents have often included ultraviolet brighteners designed to give clothes a whiter appearance upon washing. While a whiter appearance can be considered a positive selling point for the average consumer, for the hunter seeking to blend into the forest, using such products only compounds the problem of camouflage. An entire industry has developed to produce fabric dyes and detergents that are themselves not visible in ultraviolet light or mute ultraviolet signatures in existing products.

While all the aforementioned prior art seeks to avoid detection by animals capable of seeing ultraviolet light, there is little in the prior art directed towards using an animal's ability to see ultraviolet light as an attractant.

Published Patent Application 2007/0199228 to Johnson (formerly U.S. patent application Ser. No. 11/711,409) describes a decoy with a surface reflection that closely matches the spectral reflectance of the animal it is designed to mimic, including both human-visible and ultraviolet wavelengths in order to make the decoy appear more realistic to the target animals.

However, this reference is limited in scope insofar as it only teaches the use of ultraviolet reflectance for lifelike mimicry. The prior art publication is silent about the use of ultraviolet reflectance in combination with other attractant methods or the use of ultraviolet brighteners to render an object "super bright" as an animal attractant.

Thus, the need exists for solutions to the above problems with the prior art.

SUMMARY OF THE INVENTION

A primary objective of the present invention is to provide animal attractant compositions, devices, systems and methods to attract game animals by stimulating several of the animal's senses.

The novel invention includes deployable animal attractant compositions, devices, systems and methods that can be used to attract animals to a desired location using a combination of ultraviolet brighteners for visual interest and one or more of scent, salt, and motion. The invention can capitalize on the link between many animals' ability to see ultraviolet light with their desire to visualize urine territory markers left by other animals of the same species.

Further objects and advantages of this invention will be apparent from the following detailed description of the presently preferred embodiments which are illustrated schematically in the accompanying drawings.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

The present invention can include a base substrate, an ultraviolet brightener, and, optionally, one or more additional attractants such as animal scent, salt, and motion.

The base substrate can be fashioned into any geometry, but most advantageously such a geometry should not approximate naturally occurring shapes such as animals or plants. One such preferred geometry can include an elongated, flat, rectangular plate roughly the size and shape of a common paint stirring stick. Another geometry can be an irregular, unnatural shape such as several cojoined circular disks. These and other geometries when hung from a tree branch by a lanyard, can flutter and move in the breeze in a manner that piques an animal's curiosity with pleasing, natural motion while not appearing threatening. A nonthreatening yet unnatural looking object draws visual attention from far away.

The base substrate can be composed of, but not limited to, thermoplastics, thermosets, wood, and metal. Thermoplastics are preferred for their easy manipulation plus the ability to incorporate additives, such as pigments and ultraviolet brighteners into the molten plastic instead of applying them as a surface treatment. The substrate can be fashioned by physical methods common in the art such as molding of molten materials or machining from rough stock.

In one embodiment, the base substrate can be fabricated from a brightly-colored material to make it visible from great distances by a human observer or hunter. The substrate also incorporates an ultraviolet brightener, defined as a pigment, dye, or surface treatment that renders the base substrate brightly visible in near ultraviolet light (~200 to ~400 nanometer wavelength). This can be a key feature of the invention. One such commercially available optical brightener can include but is not limited to 2,2'-(2,5-thiophenediyl) bis (5-tert-butylbenzoxazole), trade named Benetex® OB (CAS #7128-64-5) and manufactured by Mayzo Corporation.

In the preferred embodiment, the base substrate can be fabricated from a flexible, porous ethylene vinyl acetate (EVA) copolymer that can be charged with a natural or synthetic animal scent attractant. The scent attractant can include, but is not limited to, any combination of animal attractant oil secretion, musk, urine, pheromone, preorbital gland secretion, and a proprietary synthetic attractant.

In one embodiment, the scent attractant can be packaged separately from the base substrate. Just prior to deployment, the scent attractant can include a liquid, aerosol, or semi-solid, and can be applied to the outer surface of the base substrate. The At periodic intervals (daily, weekly, etc.), the base substrate can be recharged with the scent material.

Many wild animals also crave salt. The base substrate of the present invention can be impregnated or coated with crystalline salt, typically sodium chloride, as a way of enticing wild animals to repeatedly return to the invention. While scents may attract animals once, their dietary need for salt will condition them to return regularly.

Table 1A shows the mixture components for liquid deer scent and liquid UV brightener.

TABLE 1A

| Mixture Components | Range Amounts or percentages | Preferred Range |
| --- | --- | --- |
| Liquid Deer Scent | Any amount (for example 100 ml) | Any amount (for example 100 ml) |
| Liquid (Aqueous all) Uv Brightener | Approximately 1-30 mL (or a 1%-30% Liquid UV Brightener to Liquid Deer Scent) | Approximately 20-30 mL (or a 20%-30% Liquid UV Brightener to Liquid Deer Scent) |

Liquid Deer Scent can include deer urine based scents including but not limited to doe urine, buck urine, mixed urine, doe-in-heat urine, doe-in-estrus urine, rutting buck, and the like. RuttingBuck can include urine collected from genetically superior breeding bucks. This urine, which contains a high concentration of testosterone, attracts dominant bucks.

Liquid UV Brightener can include UV tracer dyes or UV dyes. For our test subject we used UV tracer dyes from Risk Reactor of Santa Ana, Calif. Other companies make tracer dyes and dyes also that can be used.

We found that the Liquid UV Brightener should be added to the Liquid Deer scent and mixed as the UV brightener is introduced. Room temperature seems to work best. Once the deer scent and liquid UV brightener were mixed in correct amounts the deer scent would "fluoresce" when exposed to black or UV light. In consumer use the consumer will need to agitate, stir or shake the mixture to ensure proper mixing. The mixture should be stored in a dark tinted bottle to prevent breakdown of the UV enhancers.

Table 1B lists components for mixing liquid deer scent with a powder (dry) form UV brightener.

TABLE 1B

| Mixture Components | Range Amounts or percentages | Preferred Range |
| --- | --- | --- |
| Liquid Deer Scent | 100 mL for example | 100 mL, for example |
| Powder form UV Brightener | Approximately 1-30 grams (per every 100 ml) | Approximately 15-25 grams (per every 100 ml) |

Liquid Deer Scent can include deer urine, including but not limited to doe urine, buck urine, mixed urine, doe-in-heat urine, doe-in-estrus urine, rutting buck, and the like. All urine based scent used for attracting deer.

Powder or dry form UV Brightener can include any number of powder or crystalline UV brightener or whitening agents. For our test subject we used a Fluorescent Whitening agent called Benetex OB-M1 in which the chemical name is cited in the application.

We found that the Powder or dry form UV Brightener should be added to the Liquid Deer scent and mixed as the UV brightener is introduced. Room temperature seems to work best. Once the deer scent and powder/dry form UV brightener were mixed in correct amounts the deer scent would "fluoresce" under black or UV light. In consumer use the consumer will need to agitate, stir or shake the mixture to ensure proper mixing. The mixture should be stored in a dark tinted bottle to prevent breakdown of the UV enhancers.

Table 2A shows the mixture compositions of liquid food attractant scent and liquid brightener.

TABLE 2A

| Mixture Components | Range Amounts or percentages | Preferred Range |
| --- | --- | --- |
| Liquid Food Attractant Scent | 100 mL, for example | 100 mL, for example |
| Liquid UV Brightener | Approximately 1-30 mL(or a 1%-30% Liquid UV Brightener to Liquid Food Scent) | Approximately 20-30 mL (or a 20%-30% Liquid UV Brightener to Liquid Food Scent) |

Liquid (Aqueous) Food Attractant Scent can include any scent that attracts game animals in particular deer. Examples would be scents such as liquid mixtures of edible foods, such as mixing ground up versions of edible foods into water, and the like. The edible foods can be selected from at least one of: acorn, corn, beets, apples, pears, persimmons, clovers, grasses, grains, and the like. There is a wide variety of liquid scent used to attract deer.

Liquid UV Brightener can include UV tracer dyes or UV dyes. For our test subject we used UV tracer dyes from Risk Reactor, as well as several other companies make tracer dyes and dyes also.

We found that the Liquid UV Brightener should be added to the Liquid Food scent and mixed as the UV brightener is introduced. Room temperature seems to work best. Once the food scent and liquid UV brightener are mixed in correct amounts the deer scent would "fluoresce" under black or UV light. In consumer use the consumer will need to agitate, stir or shake the mixture to ensure proper mixing. The mixture should be stored in a dark tinted bottle to prevent breakdown of the UV enhancers.

Table 2B shows the mixture components for liquid food scent and dry UV brighteners.

TABLE 2B

| Mixture Components | Range Amounts or percentages | Preferred Range |
| --- | --- | --- |
| Liquid Food Attractant Scent | 100 mL, for example | 100 mL, for example |
| Powder form UV Brightener | Approximately 1-30 grams, per every 100 ml | Approximately 15-25 grams per every 100 ml |

Liquid Food Scent can include any scent that attracts game animals in particular deer. Examples would be scents from liquified versions of foods that can be selected from at least one of acorn, corn, beets, apples, pears, persimmons, clovers, grasses, grains, and the like. There is a wide variety of liquid scent used to attract deer Powder or dry form UV Brightener can include any number of powder or crystalline UV brightener or whitening agents. For our test subject we used a Fluorescent Whitening agent called Benetex OB-M1 in which the chemical name is cited in the application We found that the Powder or dry form UV Brightener should be added to the Liquid Food scent and mixed as the UV brightener is introduced. Room temperature seems to work best. Once the food scent and powder, dry form UV brightener were mixed in correct amounts the deer scent would "fluoresce" under black or UV light. In consumer use the consumer will need to agitate, stir or shake the mixture to ensure proper mixing. The mixture should be stored in a dark tinted bottle to prevent breakdown of the UV enharicers.

Table 3A shows the mixture components of dry food attractants that can include consumable foodstuff having a food value, especially a nutrient such as fat or protein, with a liquid brightener.

TABLE 3A

| Mixture Components | Range Amounts or percentages | Preferred Range |
|---|---|---|
| Dry Food Attractant | Any weight | Any weight |
| Liquid UV Brightener | Approximately 1%-30% mixture by weight | Approximately 20% to 30% mixture by weight |

Dry Food Attractants can include any food product that attracts game animals and that they may eat. Examples would be: acorns, corn, beets, apples, pears, persimmons, clovers, grasses, alfalfas, grains, beans, soybeans, turnips, and the like. There is a wide of dry food attractants used as bait for deer.

Liquid UV Brightener can include UV tracer dyes or UV dyes. For our test subject we used UV tracer dyes from Risk Reactor but several other companies make tracer dyes and dyes also.

The Liquid UV Brightener can be added as a supplement to the Dry Food Attractant just prior to taking the attractant to the field or in the field. The Liquid UV Enhancer can also be added to the Dry Food Attractant in the manufacturing process as long as precautions are made during packaging that there will be no leakage. The Mixture can also be thoroughly mixed by placing in a container and shaking or agitating. The container can be as simple as a bucket, bag, or other mixing container.

Table 3B shows the mixture components of dry food attractant with dry UV brightener.

TABLE 3B

| Mixture Components | Range Amounts or percentages | Preferred Range |
|---|---|---|
| Dry Food Attractant | Any weight | Any weight |
| Dry or Powder Form UV Brightener | Approximately 1% to 30% mixture by weight | Approximately 20%-30% mixture by weight |

Dry Food Attractants can include any food product that attracts game animals and that they may eat. Examples would be: acorns, corn, beets, apples, pears, persimmons, clovers, grasses, alfalfas, grains, beans, soybeans, turnips, etc. There is a wide of dry food attractants used as bait or attractant for deer. This includes any food that a deer may ingest both naturally occurring and placed by man. Examples are cited above.

Powder or dry form UV Brightener can include any number of powder or crystalline UV brightener or whitening agents. For our test subject we used a Fluorescent Whitening agent called Benetex OB-M1 in which the chemical name is cited in the application The Dry or Powder Form UV Brightener can be added as a supplement to the Dry Food Attractant just prior to taking the attractant to the field or in the field. The Dry or Powder Form UV Brightener can also be added to the Dry Food Attractant in the manufacturing process by mixing thoroughly in a mixer or by hand. Mixture can also be thoroughly mixed by placing in a container and shaking or agitating. The container can be as simple as a bucket, bag, or other mixing container.

Table 4A shows the mixture components of dry food attractant and liquid UV brightener.

TABLE 4A

| Mixture Components | Range Amounts or percentages | Preferred Range |
|---|---|---|
| Dry Mineral or Salt Attractant | Any weight | Any weight |
| Liquid UV Brightener | Approximately 1%-30% mixture by weight | Approximately 20%-30% mixture by weight |

Dry Mineral or Salt Attractant can include any mineral or salt type product used to attract deer and other big game animals. There are many varieties of mixtures with trace minerals, minerals, salts, and the like. These can include but are not limited to deer lick salts, deer minerals, and attractants with a salt base. Primarily available in 2 forms which are loose powder salt or mineral or in a salt or mineral block.

Liquid UV Brighteners can include UV tracer dyes or UV dyes. For our test subject we used UV tracer dyes from Risk Reactor but several other companies make tracer dyes and dyes also.

The Liquid UV Brightener can be added as a supplement to the Dry Mineral or Salt Attractant just prior to taking the attractant to the field or in the field. The Liquid UV Enhancer can also be added to the Dry Mineral or Salt Attractant in the manufacturing process as long as precautions are made during packaging that there will be no leakage. The Mixture can also be thoroughly mixed by placing in a container and shaking or agitating. The container can be as simple as a bucket, bag, or other mixing container.

Table 4B shows the mixture components of dry food attractants and dry UV brighteners.

TABLE 4B

| Mixture Components | Range Amounts or percentages | Preferred Range |
|---|---|---|
| Dry Mineral or Salt Attractant | Any weight | Any weight |
| Dry or Powder Form UV Brightener | Approximately 1%-30% mixture by weight | Approximately 20%-30% mixture by weight |

Dry Mineral or Salt Attractant can include any mineral or salt type product used to attract deer and other big game animals. There are many varieties of mixtures with trace minerals, minerals, salts, and the like. These can include but are not limited to deer lick salts, deer minerals, and attractants with a salt base. Primarily available in 2 forms which are loose powder salt or mineral or in a salt or mineral block.

Powder or dry form UV Brightener can include any number of powder or crystalline UV brightener or whitening agents. For our test subject we used a Fluorescent Whitening agent called Benetex OB-M1 in which the chemical name is cited in the application The Dry or Powder Form UV Brightener can be added as a supplement to the Dry Mineral or Salt Attractant just prior to taking the attractant to the field or in the field. The Dry or Powder Form UV Brightener can also be added to the Dry Mineral or Salt Attractant in the manufacturing process by mixing thoroughly in a mixer or by hand. Mixture can also be thoroughly mixed by placing in a container and shaking or agitating. The container can be as simple as a bucket, bag, or other mixing container.

Table 5A shows the mixture components of a gel form deer scent and liquid brightener.

TABLE 5A

| Mixture Components | Range Amounts or percentages | Preferred Range |
| --- | --- | --- |
| Gel Form Deer Scent | Any wt | Any wt |
| Liquid UV Brightener | Approximately 1%-30% mixture by volume | Approximately 20%-30% mixture by volume |

The Gel Form Deer Scent can include gels with deer urine, including but not limited to doe urine, buck urine, mixed urine, doe in heat urine, doe in estrus urine, rutting buck, and the like. All urine based scent used for attracting deer.

Liquid UV Brightener can include UV tracer dyes or UV dyes. For our test subject we used UV tracer dyes from Risk Reactor but several other companies make tracer dyes and dyes also.

We found that the Liquid UV Brightener should be added to the Gel From Deer scent during gel formation during the manufacturing process. Room temperature seems to work best. No consumer mixing is needed. The mixture should be stored in a dark tinted bottle to prevent breakdown of the UV enhancers.

Table 5B shows the mixture components for Gel Deer Scent and Dry UV brightener.

TABLE 5B

| Mixture Components | Range Amounts or percentages | Preferred Range |
| --- | --- | --- |
| Gel Form Deer Scent | any | any |
| Powder form UV Brightener | Approximately 1%-30% mixture by weight | Approximately 20%-30% mixture by weight |

Gels can include but are not limited to Hydrogels, Organogels, Xerogels, and the like. Gel Form Deer Scent can include gels with deer urine, including but not limited to doe urine, buck urine, mixed urine, doe in heat urine, doe in estrus urine, rutting buck, and the like. All urine based scent used for attracting deer.

Powder or dry form UV Brightener can include any number of powder or crystalline UV brightener or whitening agents. For our test subject we used a Fluorescent Whitening agent called Benetex OB-M1 in which the chemical name is cited in the application We found that the Powder or Dry Form UV Brightener should be added to the Gel From Deer scent during gel formation during the manufacturing process. Room temperature seems to work best. No consumer mixing is needed. The mixture should be stored in a dark tinted bottle to prevent breakdown of the UV enhancers.

The invention can include different mixture compositions that combine animal attractants and a UV brightener together. The mixture compositions can be clear and colorless, and be packaged in small jars, and the like.

The UV brightener used can be any color and must be scent free, since a scent or fragrance would change the affect of the attractant.

The novel compositions can be stored in small glass bottles, such as dark tinted bottles, ranging size from small bottles of approximately ½ ounce to approximately 4 ounces. Larger containers can be up to 1 to 5 gallons.

Dry versions of the attractant be based on bags that are sized from approximately 5 to 50 pounds.

Other types of delivery systems can also be used for the novel compositions, such as but not limited to foams, aerosolized applications, vaporized applications, misted applications, fumes, dusts, powders, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. An animal attractant composition consisting of:
   an animal attractant substance, wherein the animal attractant substance includes an edible food attractant selected from at least one of acorn, corn, beets, apples, pears, persimmons, clovers, grasses, and grains; and
   a UV (ultraviolet) brightener mixed with the animal attractant component to render the animal attractant substance brightly fluorescent in near ultraviolet light, wherein the UV brightener includes liquid brightener of approximately 20% to approximately 30% per weight of the attractant composition, wherein near ultraviolet light is defined as light with a wavelength of between about 200 and 400 nanometers, and the ultraviolet brightener attracts animals to where the animal attractant substance is located.

2. An animal attractant composition consisting of:
   an animal attractant substance, wherein the animal attractant substance includes deer scent selected from the group consisting of doe urine, buck urine, mixed urine, doe-in-heat, doe-in-estrus, and rutting buck; and
   a UV (ultraviolet) brightener mixed with the animal attractant component to render the animal attractant substance brightly fluorescent in near ultraviolet light, wherein the UV brightener includes liquid brightener of approximately 20% to approximately 30% per weight of the attractant composition, wherein near ultraviolet light is defined as light with a wavelength of between about 200 and 400 nanometers, and the ultraviolet brightener attracts animals to where the animal attractant substance is located.

3. The animal attractant composition of claim 2, wherein the UV brightener includes a powder brightener of approximately 1 gram to approximately 30 grams for every 100 ml of liquid deer scent per weight of the attractant composition.

4. The animal attractant composition of claim 3, wherein the UV brightener includes a powder brightener of approximately 15 grams to approximately 25 grams for every 100 ml of liquid deer scent per weight of the attractant composition.

5. The animal attractant composition of claim 1, wherein the UV brightener includes powder brightener of approximately 1 gram to approximately 30 grams for every 100 ml of liquid deer scent per weight of the attractant composition.

6. The animal attractant composition of claim 5, wherein the UV brightener includes a powder brightener of approximately 15 grams to approximately 25 grams for every 100 ml of liquid deer scent per weight of the attractant composition.

7. The animal attractant composition of claim 1, wherein the edible food attractant includes a liquified edible food attractant.

8. The animal attractant composition of claim 1, wherein the edible food attractant includes a dry edible food attractant.

9. The animal attractant composition of claim 2, wherein the deer scent is selected from a gel deer scent or a liquid deer scent.

10. A packaged deer attractant, comprising:
- an attractant composition consisting of an deer attractant substance, selected from at least one of a deer urine based scent or a deer edible food scent; and
- a UV (ultraviolet) brightener mixed with the deer attractant substance to form a mixture that is brightly fluorescent in near ultraviolet light, wherein the UV brightener includes liquid brightener of approximately 20% to approximately 30% per weight of the attractant composition, wherein near ultraviolet light is defined as light with a wavelength of between about 200 and 400 nanometers, and the ultraviolet brightener attracts animals to where the animal attractant substance is located; and
- a dark tinted container for storing the mixture.

* * * * *